(12) United States Patent
Schleifer et al.

(10) Patent No.: US 8,490,466 B2
(45) Date of Patent: Jul. 23, 2013

(54) CAPSULE INJECTION SYSTEM FOR GAS CHROMATOGRAPHY

(75) Inventors: Arthur Schleifer, Portola Valley, CA (US); Carl A. Myerholtz, San Jose, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 540 days.

(21) Appl. No.: 12/642,843

(22) Filed: Dec. 20, 2009

(65) Prior Publication Data

US 2011/0146380 A1  Jun. 23, 2011

(51) Int. Cl.
- *G01N 1/22* (2006.01)
- *G01N 1/28* (2006.01)
- *G01N 30/06* (2006.01)

(52) U.S. Cl.
USPC ... 73/23.41; 73/23.37; 73/863.11; 73/864.74; 73/864.82

(58) Field of Classification Search
USPC ............ 73/23.37, 23.41, 863.11, 863.74, 73/864.81, 864.82, 864.74
See application file for complete search history.

(56) References Cited

U.S. PATENT DOCUMENTS

| | | | | |
|---|---|---|---|---|
| 3,002,387 A | * | 10/1961 | Micheletti | 73/864.82 |
| 3,063,286 A | * | 11/1962 | Nerheim | 73/23.41 |
| 3,498,107 A | | 3/1970 | Kim et al. | |
| 3,672,227 A | * | 6/1972 | Frank et al. | 73/864.82 |
| 3,730,002 A | * | 5/1973 | Penton | 73/864.82 |
| 3,759,107 A | | 9/1973 | Fox et al. | |
| 3,783,694 A | * | 1/1974 | Otte et al. | 73/864.74 |
| 4,226,119 A | * | 10/1980 | Buser | 73/864.82 |
| 4,533,641 A | * | 8/1985 | Holt | 436/43 |
| 5,686,656 A | * | 11/1997 | Amirav et al. | 73/23.41 |
| 2005/0056970 A1 | * | 3/2005 | Foust | 264/482 |
| 2005/0152969 A1 | * | 7/2005 | Chiprich | 424/456 |

FOREIGN PATENT DOCUMENTS

| | | |
|---|---|---|
| WO | 01/88525 A1 | 11/2001 |
| WO | 03/060508 A2 | 7/2003 |

OTHER PUBLICATIONS

European Search Report, EP 10190372.2-2204, Mar. 10, 2011, all pages Ehmann W.D., McKown D.M.: "Heat-Sealed Polyethylene Sample Containers for Neutron Activation Analysis", Analytical Chemistry, vol. 40, No. 11, Sep. 1968, pp. 1758-1759.

* cited by examiner

*Primary Examiner* — Daniel Larkin

(57) ABSTRACT

The present invention includes a heat sealable capsule adapted for use in analysis devices such as GCs, and methods for using the capsules to perform analysis in such devices. The capsules include a tube having an end that is heat-sealed to contain a sample that is to be analyzed at an injection temperature. The tube includes a heat sealable medium having a heat seal that closes the end, the tube having an inner and outer surface, both of the surfaces being substantially chemically inert with respect to the sample. The tube is substantially free of any material that outgases at the injection temperature. The tube is openable without breaking into pieces, and remains intact at the injection temperature. The capsule can include a programmable tag that stores information related to the sample contained therein.

7 Claims, 8 Drawing Sheets

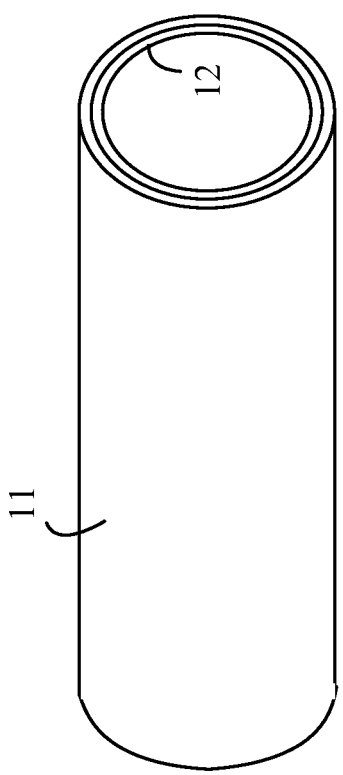
FIGURE 1
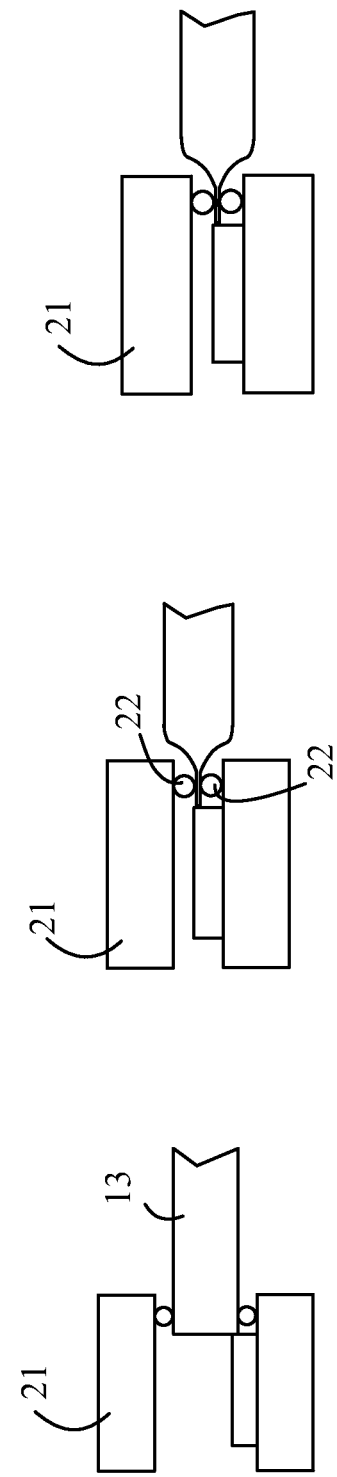
FIGURE 2C
FIGURE 2B
FIGURE 2A

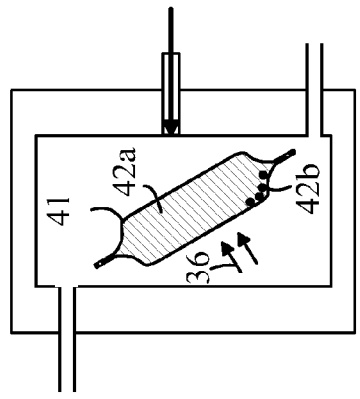
FIGURE 3A
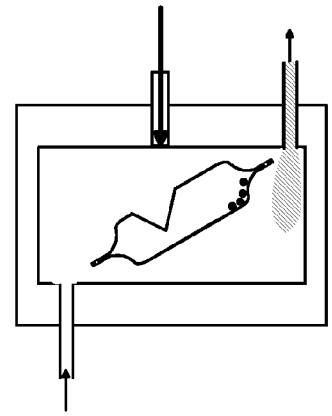
FIGURE 3B
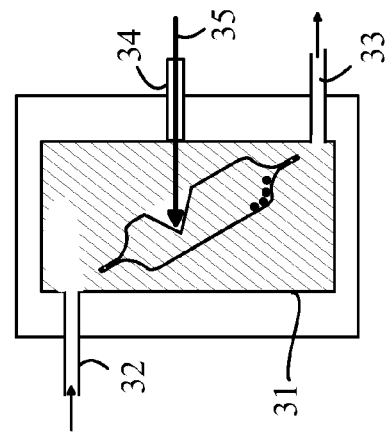
FIGURE 3C
FIGURE 3D

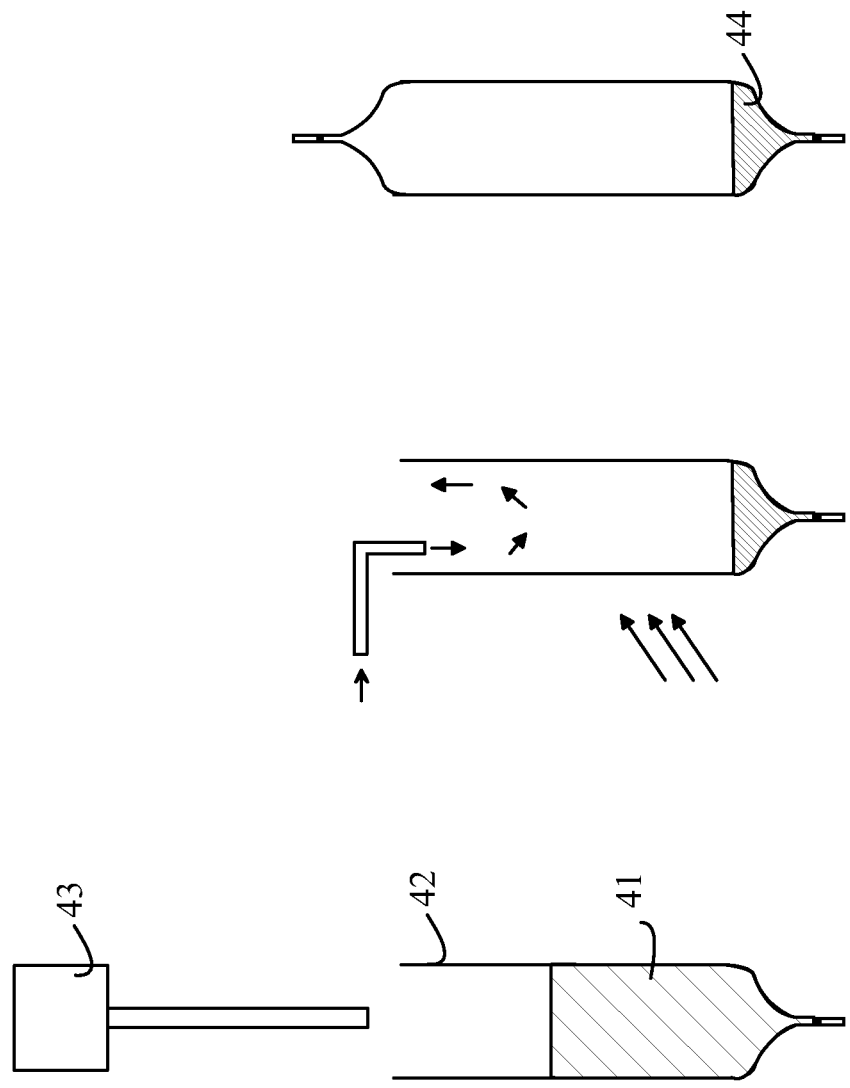

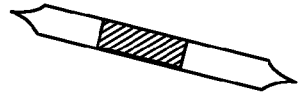
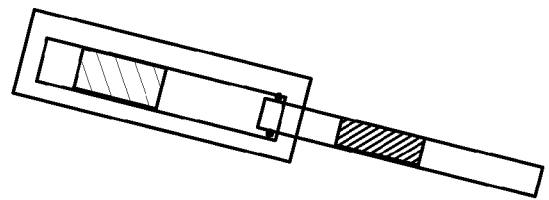
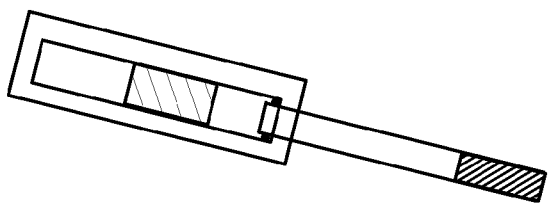
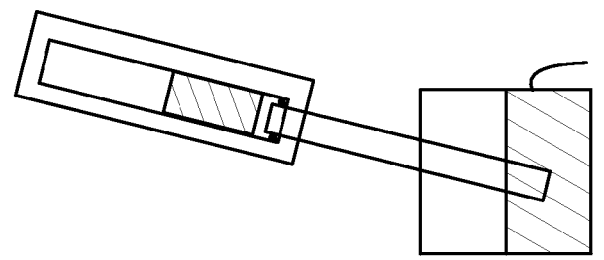
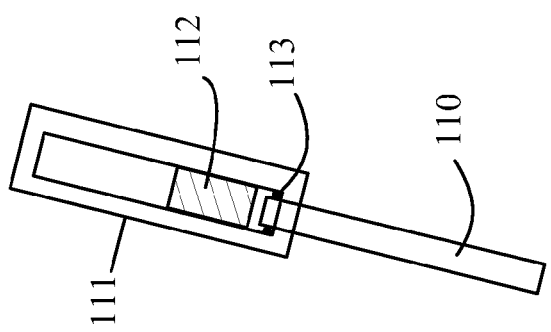

CAPSULE INJECTION SYSTEM FOR GAS CHROMATOGRAPHY

BACKGROUND OF THE INVENTION

Gas chromatography (GC) is used to separate and analyze compounds that can be vaporized without undergoing degradation. Typically, a sample containing a number of components to be analyzed is moved through a column via a carrier gas. The packing material, or walls of the column contain a chemical(s) that interacts with the components in the sample, such that different components move through the column at different rates of speed. Hence, the different components of the sample are eluted from the sample at different times even though all of the components entered the column at the same time. The performance of the GC depends on a mechanism for introducing the sample into the gas flow over a short period of time without significantly disturbing the gas flow.

For samples that are not gases at room temperature, a mechanism is needed to heat the sample to the vapor phase and then introduce that gas into the GC column over a short period of time. Injection ports on GCs are maintained at an elevated temperature so that when a liquid sample is injected, the solvent and sample(s) dissolved in the solvent, are vaporized. There is a balance between having the injection temperature high enough to vaporize the sample rapidly, but not too high as to thermally degrade any of the components of the sample. Liquid samples are typically injected into the injection port with a syringe and needle. The needle of the syringe pierces the septum on the injection port and the plunger of the syringe is depressed, forcing the liquid sample into the injection port. Automated injectors generally provide more consistent results than injection schemes based on manual injection of the sample. However, neither of these schemes lends itself to the processing of solid samples. In addition, injection ports will typically discriminate during the injection process. That is, lower boiling point solvents and sample(s) will vaporize earlier than higher boiling point compounds. Also, depending on the injection technique and injection port design, the solvent and sample(s) will vaporize at different times, resulting in a broader than desired sample solvent plume entering the column. As a result, different injectors are required for different types of samples and different types of analysis.

Injection techniques based on samples that have been previously packaged into capsules, in principle, can overcome many of these problems. In such systems, the sample is placed in a capsule and sealed. The sealed capsule is introduced into a chamber in the GC where it is heated to the desired temperature to volatilize the sample and then opened quickly in the gas stream. This arrangement allows a single type of injector to handle different types of samples. In addition, only the capsule loading apparatus need be located at the sampling site, and hence, the problems associated with remote monitoring are greatly reduced. Unfortunately, prior art capsules for use in such systems have had significant problems that limit this type of GC system.

The ideal capsule must satisfy a number of criteria. First, the capsules must be capable of being loaded and sealed without vaporizing the sample being loaded into the capsule. Second, the sealing mechanism must be easily implemented in a cost-effective manner. Third, the capsules must be chemically inert and non-volatile at the temperatures used to vaporize the samples. Fourth, the capsules must be easily punctured within the GC to release the volatile contents of the capsule. Finally, the spent capsules must be easily removed from the GC.

Unfortunately, prior art capsules differ significantly from this ideal, which has limited their use. Prior art capsules for use in GCs are typically constructed from metal or a glass. Metal capsules constructed from gold, indium, or aluminum, are known to the art. Metal capsules present problems in terms of sealing the sample in the capsule. In general, the capsule end is either closed by a crimping operation or welded shut after introducing the sample into the capsule. Crimp seals can appear closed even when the seal has a small leak. For a solid or liquid sample, the leak may not become evident until the capsule is heated in the GC. Such a capsule will release the contents over an extended period of time before the capsule is actually punctured. Welding also presents problems. Since the metals are good heat conductors, the heat generated by the welding operation at one end of the capsule can be transferred to the sample during the welding operation and cause part of the sample to vaporize and escape before the weld is complete.

Most metals are not chemically inert at the temperatures at which the samples are vaporized. Those that are relatively inert, such as gold, are expensive. In addition, metals that melt at the injection temperature leave material in the inlet that is difficult to remove.

Glass capsules provide improvements in terms of chemical inertness and cost. However, these capsules are difficult to seal and leave small pieces of glass behind after opening that are difficult to remove from the inlet to the GC. Glass capsules are typically glass capillaries with inner diameters of around 1 mm and closed on one end. Samples are placed in the glass capillary and then sealed with a flame. The sealed glass capillary is placed in the heated zone of the inlet to the GC and allowed to come to temperature. Once at temperature, the capillary is broken and the volatile contents released and the carrier gas would sweep the volatiles into the inlet to the GC.

Sealing of the glass capillary using a flame requires expertise on the part of the user and is not easily automated. Furthermore, during the sealing process, the capillary is heated, and heat can be transferred to the sample causing volatiles to escape. Another problem with sealing the glass capsule using heat or flame is that even when the end of the capsule is sealed, the glass remains at an elevated temperature and in a softened state for some time. The residual heat can be transferred to the solvent in the capsule causing the solvent to vaporize and pressurize the capsule leading to the softened glass seal failing. Finally, as noted above, when the glass capillary is broken in the inlet, small pieces of glass that are difficult to remove are generated.

SUMMARY OF THE INVENTION

The present invention includes a heat sealable capsule adapted for use in GCs, GCs utilizing the same, and methods for using the capsules to perform analysis in GCs. The capsules include a polymeric tube having first and second ends that are heat-sealed to contain a sample that is to be analyzed at an injection temperature. The tube includes a heat sealable medium having a first end that is closed, the tube having an inner and outer surface, both of the surfaces being substantially chemically inert with respect to the sample. In addition, the tube is substantially free of any material that outgases at the injection temperature. The capsule may include an absorbent matrix that immobilizes the sample at a temperature below the injection temperature. In one aspect of the invention, the tube includes an organic polymer. In another aspect of the invention, the capsule includes a programmable RF identification (RFID) tag. The RFID tag can be sealed in a separate compartment on or in the capsule.

A sample to be analyzed is placed in the tube and the ends of the tube are heat-sealed. The heat-sealed capsule is placed in a sample injection chamber of an analysis device and heated to an injection temperature at which components of the sample are in a gaseous phase. The heated capsule is then opened and a carrier gas is used to sweep the gaseous phase components into the analysis device for analysis. In one aspect of the invention, the capsule is opened by piercing the capsule. In another aspect of the invention, the capsule is opened by mechanically compressing or squeezing the capsule, which causes the heat seal area or the material to fail and open. In another aspect of the invention, identification information associated with the capsule is read from the capsule and associated with the measurements made in the analysis device.

BRIEF DESCRIPTION OF THE DRAWINGS

FIG. 1 illustrates a capsule according to the present invention prior to the capsule being sealed.

FIGS. 2A-2C illustrate one method for sealing the capsule after a sample has been introduced into the capsule.

FIGS. 3A-3D illustrate the manner in which a capsule according to one embodiment of the present invention is used to process a sample via a capsule injection chamber.

FIGS. 4A-4C illustrate the removal of the solvent from a capsule prior to closing the sample.

FIGS. 10A-10E illustrate the manner in which the capsules are filled and sealed according to one embodiment of the present invention.

DETAILED DESCRIPTION OF THE PREFERRED EMBODIMENTS OF THE INVENTION

Figure 2E:
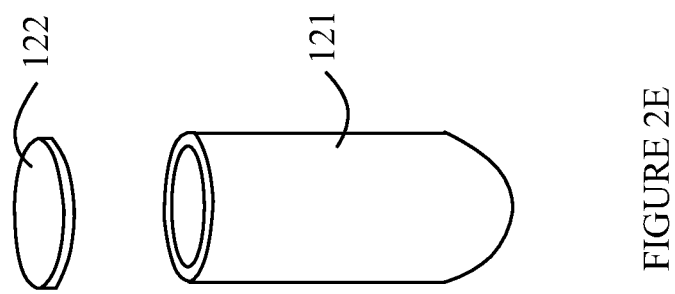
FIGS. 2D and 2E illustrate two capsules according to two other embodiments of the present invention.

The ideal capsule for use with capsule injection based GCs or similar devices should have a number of characteristics. First, the capsule should be constructed from a material that is chemically inert at the temperatures employed to vaporize the sample. In some embodiments, the capsule can withstand a temperature of 300° C. The capsule material should not have significant out-gassing at these temperatures.

Second, the capsule must have minimal vapor transmission until the capsule is opened in the inlet of the GC. As noted above, vapor transmission before the capsule is opened leads to degradation of the GC analysis.

Third, the capsule must be easy to seal and easily opened in the GC to allow the vapor to escape. A sealing system that requires inexpensive equipment that does not require a high degree of operator skill is preferred.

Fourth, the spent capsule must be easily removed from the GC. Hence, materials that melt at the vaporization temperature or shatter during the opening process are unsatisfactory.

Fifth, the capsule should have a low thermal mass and a low thermal resistance. The time needed to transfer heat to the capsule to vaporize the sample can be significant. This heating time can increase the analysis time, and hence, reduce the sample throughput in the GC.

Finally, the capsules should be inexpensive.

Refer now to FIG. 1, which illustrates a capsule according to the present invention prior to the capsule being sealed. In one aspect of the present invention, capsules made from a polyimide tube 11 include an inner coating of fluoropolymer (FEP) 12. Polyimide and FEP are both chemically inert with respect to most samples that are candidates for processing via GC. In addition, polyimide can withstand temperatures >300° C. FEP softens at temperatures above 280° C., but can withstand higher temperatures for short time periods. Hence, polyimide capsules can withstand injection temperatures up to 280° C. or slightly higher.

Polyimide film can be formed into tubes with inner diameters ranging from 100 microns to several millimeters. The thickness of the polyimide tubes is typically between 25 microns to 150 microns. Commercially available tubes with the FEP coating on the inside of the tubing wall and, optionally, on the outside of the tube wall are available with wall thickness from 2.5 microns to 25.4 microns. The tubing can be cut into lengths appropriate for a GC injection system. This FEP coating imparts heat sealability to the tubes, provides an increased vapor barrier, and enhances the chemical resistance of the polyimide.

Refer now to FIGS. 2A-2C, which illustrate one method for sealing the capsules after a sample has been introduced into the capsule. The capsule initially consists of a polyimide tube 11 having an inner coating 12 of FEP as described above. An open end of capsule 13 is placed in the jaws of a clamp 21 as shown in FIG. 2A. The jaws of clamp 21 are then brought together to close the end of capsule 13 as shown in FIG. 2B. Clamp 21 includes heating elements 22 that apply sufficient heat to fuse the FEP coating on the inner surface of the polyimide tube. The heating element can be constructed from a resistive wire through which a current is passed. Another method to seal the capsules is ultrasonic welding. This method provides localized energy to melt the thermoplastic.

Figure 2D:
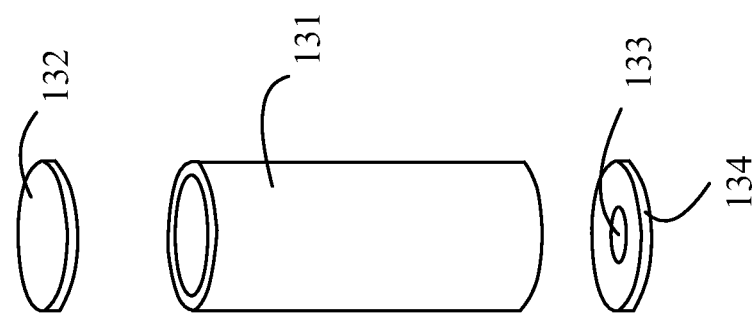

Refer now to FIGS. 2D and 2E, which illustrate two additional embodiments of a capsule according to the present invention. In these embodiments, a somewhat thicker tubular section is utilized and one or two end caps are heat sealed to the tubular section. In the embodiment shown in FIG. 2D, two end caps 132 and 134 are heat sealed to a tube 131. One of the end caps can include a device for storing information about the sample such as an RFID tag 133. In practice, one end is sealed prior to introducing the sample. The second end is then heat sealed.

In the embodiment shown in FIG. 2E, the capsule utilizes an injection molded component 121 having a closed end. A cap 122 is then heat sealed to component 121 after the sample is introduced.

It should be noted that the tubes can be loaded and sealed remotely with respect to the GC. The sealing apparatus requires very little technical expertise and is inexpensive. The sealed tubes can then be transported to a GC as a group for analysis.

The polyimide tubes have low thermal mass, and hence, do not substantially increase the time needed to bring a sample within the capsule to the injection temperature when heat is applied. For example, polyimide tubes with walls as thin as 50 microns can be utilized to provide a short thermal equilibration time. In one exemplary embodiment, the tubes have an inner diameter of approximately 3 mm and a length of 10 mm.

The tubes can be readily opened by piercing with a sharp object after being heated to the desired injection temperature. The piercing operation does not result in the tube being shattered, and hence, the capsule can be removed without leaving pieces of the capsule behind in the GC. In addition, the material does not melt at the injection temperature, and hence, does not leave residue that must be separately removed from the GC.

Refer now to FIGS. 3A-3D, which illustrate the manner in which a capsule according to one embodiment of the present invention is used to process a sample via a capsule injection chamber. Referring to FIG. 3A, sample injection chamber 30 includes a sample compartment 31 in which a sealed capsule 41 is placed. In the example shown in these figures, capsule 41 includes a sample 42, which has both volatile (i.e., low boiling point) and non-volatile (i.e., high boiling point) components. Sample chamber 31 also includes a lance port 34 through which a lance 35 can be inserted to puncture capsule 41. Sample chamber 31 includes an inlet port 32 through which a carrier gas can be introduced and an outlet port 33 that exhausts the carrier gas to the column in the GC. Sample chamber 31 also includes a sample port through which capsule 41 is introduced into sample chamber 31. To simplify the drawing, the sample port is not shown; however, it is to be understood that the sample port is sealable after capsule 41 is introduced into sample chamber 31.

After capsule 41 is placed in sample chamber 31, capsule 41 is heated via a heater, and heated carrier gas, that is also part of sample chamber 31, as indicated by the arrows shown at 36 in FIG. 3B. As a result of the heating, the volatile components of sample 42 are vaporized and fill the interior of capsule 41 as shown at 42a. The non-volatile components remain in the capsule 41 as shown at 42b. Since all of the volatile components are transformed in the gaseous state while still in capsule 41, the problems associated with the serial vaporization of components are avoided. The temperature of the injection port is set such that all compounds of interest will be transformed to the vapor phase, but the temperature will not be set too high as to result in thermal degradation of the compounds of interest.

Refer now to FIG. 3C. After the contents of capsule 41 have been heated to the injection temperature, capsule 41 is opened using lance 35. The contents of capsule 41 are released into sample chamber 31. A carrier gas is then introduced via port 32, and the contents of sample chamber 31 are swept out of port 33 into the GC. The non-volatile components of the sample are left behind in capsule 41 as shown in FIG. 3D. These non-volatile components are removed when the spent capsule is removed, and hence, do not contaminate the GC or sample chamber. Since the non-volatile components are removed with the disposable capsule, which does not shatter or otherwise break apart when opened, problems of sample carry over between samples are significantly reduced.

It should also be noted that the present invention allows the amount of sample that is analyzed by the GC to be accurately determined. The tube can be weighed before loading the sample and after sealing the tube. Since the sealing process does not alter the weight of the capsule, the amount of sample is merely the difference in observed weights.

In one aspect of the invention, a capsule according to the present invention can be used to concentrate the sample prior to sealing the capsule. In some situations, the sample to be analyzed is only available in a dilute solution. The volume of sample/solvent needed to provide a sufficient sample is too large for processing through the GC. To reduce the volume and concentrate the sample, the solvent must be evaporated prior to vaporizing the sample itself in the GC. Methods for accomplishing this in the GC are known; however, such methods tie up the GC for a longer period of time while the solvent is evaporated and can lead to a loss of resolution in the GC.

Refer now to FIGS. 4A-4C, which illustrate one method of removing the solvent from a capsule prior to closing the sample. In this aspect of the present invention, the solvent with the dissolved sample 41 is placed in an open capsule 42 using a dispenser 43. The capsule and its contents are then heated to a temperature at which the solvent will evaporate without causing the sample to evaporate significantly as shown in FIG. 4B. The process can be aided by gently blowing an inert gas over the surface of the solvent to accelerate the rate at which the solvent is removed. When the desired amount of solvent has been removed, the capsule is sealed leaving the concentrated sample as shown at 44 in FIG. 4C.

Figure 5:
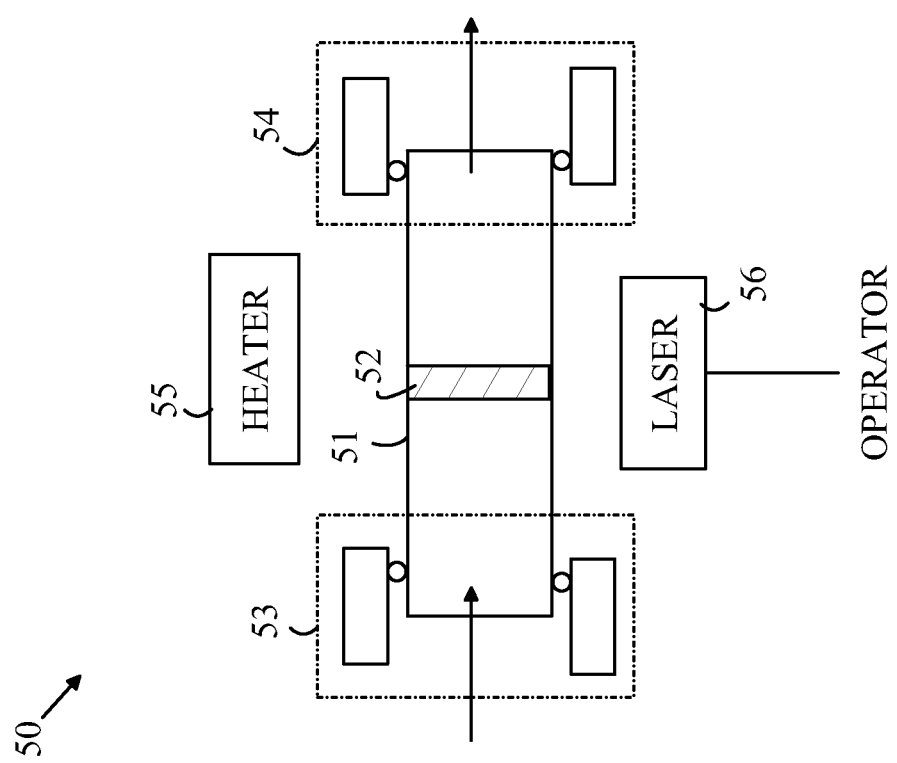
FIG. 5 illustrates an apparatus for loading and sealing a polyimide tube, with a contained section of absorbent material, into a capsule.

In another aspect of the present invention, the polyimide tube includes an absorbent matrix on which the sample can be trapped. The sample is passed through the matrix by flowing a gas or liquid through the polyimide tube containing the matrix. After the sample has been absorbed onto the matrix, the ends of the matrix are heat-sealed as described above. Refer now to FIG. 5, which illustrates an apparatus for loading and sealing a polyimide tube into a capsule. The polyimide tube 51 with an absorbent matrix 52 is positioned in a holder that includes two sealing clamps 53 and 54.

Apparatus 50 optionally includes a heater 55 that applies heat to polyimide tube 51 and absorbent matrix 52 to remove solvent from absorbent matrix 52 when the sample is loaded onto absorbent matrix 52 by passing a solvent containing the sample material through absorbent matrix 52. The removal of the solvent can be accelerated by passing an inert gas through polyimide tube 51 while absorbent matrix 52 is being gently heated. Heater 55 can be implemented to directly apply heat to polyimide tube 51 via infra red heating or microwave heating. Heater 55 can also be implemented by heating the inert gas prior to passing the gas through absorbent matrix 52.

Absorbent matrix 52 can be constructed from a large variety of materials. Exemplary materials include Tenax-TA™, Tenax-GR™, HayeSep D™, Chromsorb 106™, and Carbotrap™. In one embodiment, absorbent matrix 52 is constructed from a compressible material so that the matrix can be inserted in polyimide tube 51 and form a seal with the tube that inhibits the carrier gas or liquid from moving through polyimide tube 51 without passing through absorbent matrix 52.

In another aspect of the present invention, the capsules carry identification information that is readable by the sample chamber just prior to injection. The identification information can include a number that identifies the capsule and its contents. In one aspect of the present invention, the identification information is incorporated at the time the capsule is filled with the sample, and includes the GPS location and operator name. It should be noted that the information must be incorporated in a manner that does not provide a source of outgassing when the capsule is later heated in the sample chamber. Hence, labeling techniques based on ink printing present problems. Techniques based on laser scribing of the outer surface of the capsule avoid these problems. For example, apparatus 50 can include a laser 56 that inscribes the identification information provided by the operator on the outer surface of polyimide tube 51 during the filling and sealing process.

Figure 6:
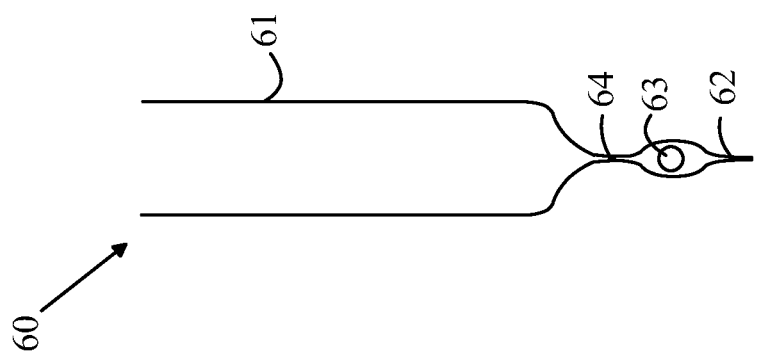
FIG. 6 illustrates an empty capsule that includes an RFID.

In another aspect of the present invention, the labeling information is provided by a programmable RF identification tag (RFID) that is incorporated in the empty capsule. Refer now to FIG. 6, which illustrates an empty capsule that includes an RFID. Capsule 60 is constructed from a heat sealable tube 61 and has two heat seals at one end of the tube as shown at 62 and 64. RFID 63 is located between the heat seals 62 and 64. Capsule 60 can be formed by first heat-sealing one end of tube 61 to form seal 62. RFID 63 is then placed adjacent to seal 62 by dropping RFID 63 into tube 61 from the open end of tube 61 while tube 61 is in the vertical position. Heat seal 64 is then formed to isolate RFID 63 from the sample chamber in capsule 60. After the sample is placed in capsule 60 and the other end sealed, RFID 63 can be programmed using an RF transmitter.

The information stored in RFID 63 can then be accessed using an RF receiver when the capsule is loaded into the GC for processing. RFIDs that are powered by an incoming RF signal do not require batteries and can withstand the heating during the sealing process. It should be noted that the RFID does not need to survive the heating in the sample chamber provided it is read prior to heating the sample.

The above-described embodiments utilize polyimide tubes that are coated with FEP; however, other materials could be utilized. The choice of tubular material depends on the type of samples that are to be encapsulated and analyzed. Ideally, the tubular material is inert at the sample injection temperatures both with respect to the sample being analyzed and with respect to out gassing at these temperatures. Since the tubular material will be exposed to the heated sample in the sample chamber after the capsule is opened, both the inner surface and outer surface of the capsule should be chemically inert with respect to the sample being analyzed. However, it should be noted that the outer surface is exposed to the sample at the injection temperature for a period of time that is typically much shorter than the time the inner surface is exposed. Hence, the degree of inertness required for the outer surface can be somewhat less than that required for the inner surface.

The tubular material must be heat sealable in a manner that does not impart a significant amount of heat to the sample. A material that has a high lateral thermal resistance is advantageous in this regard, as the heat from the sealing heater is inhibited from flowing through the tube to the sample. At the same time, however, the tubular material should not inhibit the rapid heating of the sample in the injection chamber. A thin, heat resistant material provides these functions.

The heat seal must remain intact at the sample injection temperature prior to the capsule being opened. Since the sample injection temperature depends on the samples being analyzed, different materials can be utilized to accommodate different types of samples. In some embodiments, the injection temperature is at least 220, 240, 260, 280, 300, 320 or 340° C.

The tubular material must allow the capsule to be opened without leaving behind any residue in the sample injection chamber. Hence, the tubular material should not melt or shatter upon opening.

As noted above, FEP-coated polyimide tubes satisfy these constraints for a large class of samples. In addition, such tubing is utilized for electrical insulation, and hence, is commercially available, which reduces the cost of the tubing. FEP tubing without the polyimide core can also be used for the capsules. Other materials that can be utilized include thermoplastics such as PEEK and Teflon. PEEK has a melting temperature of 340° C., and hence, can be utilized at injection temperatures of at least 300° C.

In the above-described embodiments, the capsule is opened by puncturing the capsule with a lance after the capsule has been heated to the injection temperature. While most of the volatile contents of the capsule are removed by this process, some material may still remain in the capsule and not be swept into the GC. In situations in which a quantitative result is desired, the material left behind could introduce an error into the measurement. In addition, when the sample is particularly small, the material left behind could constitute a significant fraction of the overall sample.

Figure 7:
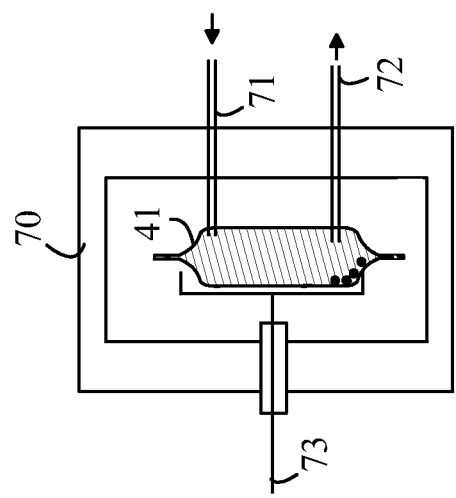
FIG. 7 illustrates another embodiment of a sample injection chamber according to the present invention.

Refer now to FIG. 7, which illustrates another embodiment of a sample injection chamber according to the present invention. Sample injection chamber 70 includes two needles 71 and 72 that penetrate capsule 41 after capsule 41 has been heated to the injection temperature. The carrier gas flows into the punctured capsule via needle 71 and out via needle 72 that is connected to the GC column. Capsule 41 is forced against needles 71 and 72 by mechanism 73 that holds capsule 41 in the desired position while forcing the capsule against the needles. Since the carrier gas actually enters the capsule and flushes out the volatile contents of the capsule, essentially, the entire sample is introduced into the GC.

Figure 8:
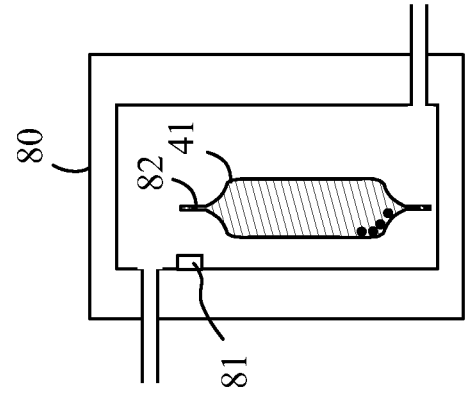
FIG. 8 illustrates a capsule injection chamber that utilizes a localized energy source to weaken the heat seal at one end of the capsule after the capsule has been heated to the injection temperature.

The above-described embodiments require some form of moveable mechanical mechanism to rupture the capsule within the sample injection chamber. However, embodiments that utilize other mechanisms to open the capsule could also be constructed. Refer now to FIG. 8, which illustrates a capsule injection chamber 80 that utilizes a localized energy source 81 to weaken the heat seal at one end of the capsule after the capsule has been heated to the injection temperature. For example, energy source 81 could be a laser 81 that illuminates heat seal 82 on capsule 41. The internal pressure within capsule 41 forces end 82 of capsule 41 open once the heat seal has been weakened or melted, and hence, no moving parts are required. In another example, the heat seal region is provided with an energy absorbent material such as a coating of a dark, chemically inert material that enhances the absorption of the laser light in the desired region. In yet another example, capsule 41 could include a metallic material in the heat seal area and energy source 81 could be a microwave source.

Figure 9:
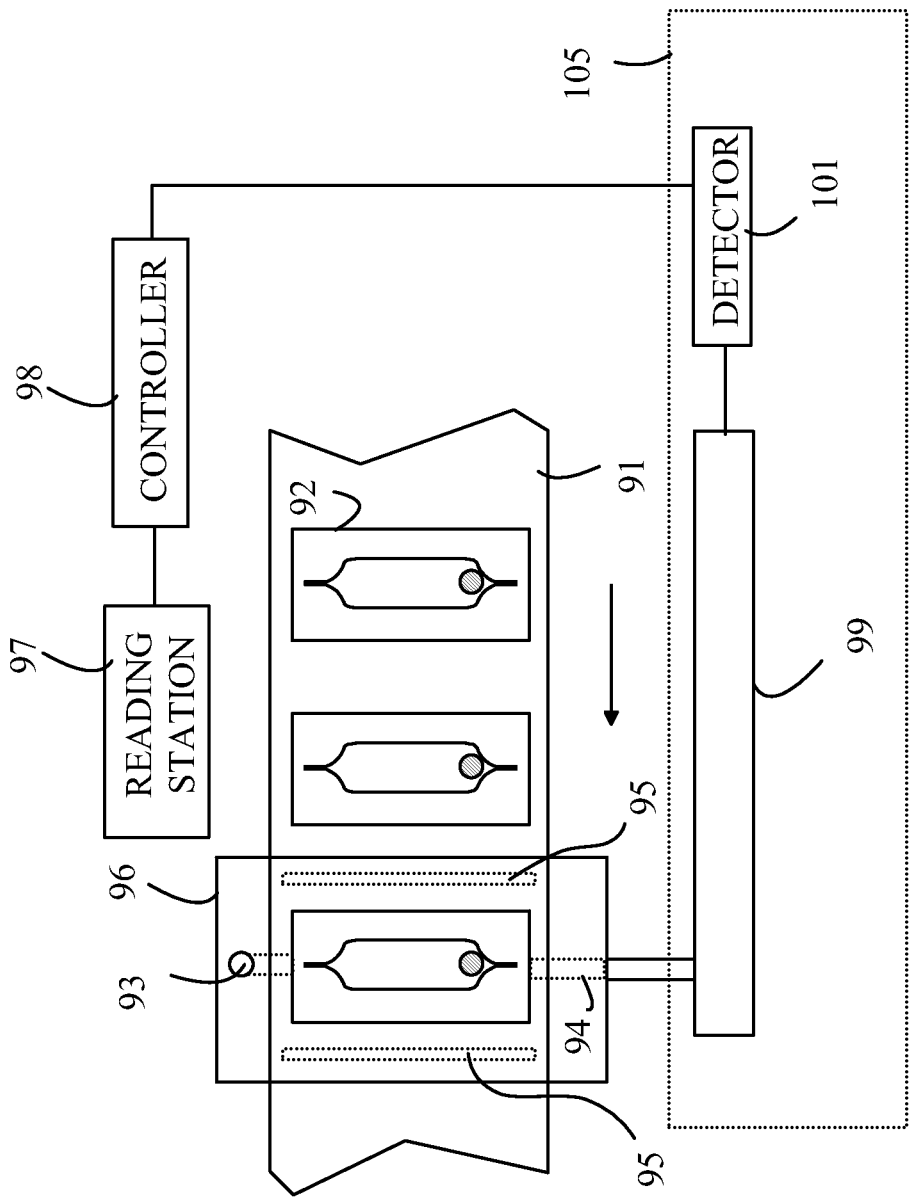
FIG. 9 illustrates one mechanism for automatically changing capsules.

A capsule injection system according to the present invention is well adapted for automated sample processing. Refer now to FIG. 9, which illustrates one mechanism for automatically changing capsules. The individual capsules to be analyzed are loaded into a carrier 91 that includes compartments 92 that hold the individual capsules. Carrier 91 moves the capsules, one at a time, into sample injection chamber 96. A set of seals 95 seal the chamber after each capsule is moved into place. As the capsules pass reading station 97, the identification information discussed above is read and transmitted to controller 98 that stores this information with the resultant GC data. Once positioned in sample injection chamber 96, the capsule is heated and the contents released as described above. In the embodiment shown in FIG. 9, carrier 91 includes passages that connect with the gas inlet and outlet ports shown at 93 and 94, respectively. Port 94 is in communication with an analysis device 105, which in this case is the separation column 99 and detector 101 of the GC. Detector 101 detects the material that is eluded from the column as a function of time and reports the results to controller 98, which associates the data with information read from the capsule.

In another embodiment, the capsule is a capillary tube fabricated from the same polymer material(s) discussed above. The capsule in this form allows the liquid sample to be drawn into the capillary, moved to the center of the capillary, and then the ends of the capillary tube are sealed to form the sealed capsule. Refer now to FIGS. 10A-E, which illustrate the sequence of operations in the filling of the capsule. The capillary tube 110 is placed in a syringe 111 and the end of the capillary is sealed to the inner chamber of the syringe with an O-ring 113 as shown in FIG. 10A. FIG. 10B shows the capillary tube inserted into a liquid sample container 114. The liquid sample is drawn into the capillary by moving the plunger 112 in the syringe. The volume of the liquid sample drawn into the capillary is determined by the area of the end of the plunger and the distance the plunger is moved as shown in FIG. 10C. After the capillary is removed from the sample container, the plunger is moved again to position the liquid sample plug in the center of the capillary, as shown in FIG. 10D. FIG. 10E shows the capillary after it is removed from the syringe and the ends have been sealed as described above.

While the present invention has been described in terms of embodiments that are adapted for use in GCs, the invention could also be utilized with other forms of analysis devices. For example, an injection chamber according to the present invention could also be utilized in an input stage to a mass spectrometer. In such applications, the separation column and detector shown in FIG. 9 would be replaced by the alternative analysis device.

The above-described embodiments refer to heat sealable tubes. For the purposes of this patent, a tube is defined to be heat sealable if an end of the tube can be sealed by applying heat to that end. The tube end can be heated directly by contact with a heater, indirectly by radiant heating, by ultrasonic welding or by microwave heating. The sealing operation can also utilize localized pressure in combination with heating to form the seal.

The above-described summary of the invention and embodiments of the present invention have been provided to illustrate various aspects of the invention. However, it is to be understood that different aspects of the present invention that are shown in different specific embodiments can be combined to provide other embodiments of the present invention. In addition, various modifications to the present invention will become apparent from the foregoing description, accompanying drawings, and the claims.

What is claimed is:

1. An apparatus comprising:
an injection chamber that receives a polymeric capsule containing a sample to be analyzed, said injection chamber comprising a mechanism for opening said polymeric capsule after said sample has been heated to a predetermined injection temperature, and a first port that is in communication with an analysis device.

2. The apparatus of claim 1 comprising a second port that receives a carrier gas that sweeps contents of said injection chamber into said first port.

3. The apparatus of claim 1 wherein said analysis device comprises a separation column.

4. The apparatus of claim 1 wherein said analysis device comprises a mass-spectrometer.

5. The apparatus of claim 2 wherein said mechanism for opening said polymeric capsule comprises first and second needles that penetrate said polymeric capsule, said first needle being connected to said first port and said second needle being connected to said second port.

6. The apparatus of claim 1 further comprising a sample loader connected to said injection chamber, said sample loader automatically loading a plurality of said polymeric capsules sequentially into said injection chamber, said sampler loader comprising an identification reader that reads information encoded in said polymeric capsules prior to said capsules being loaded into said injection chamber.

7. The apparatus of claim 1 further comprising a sample loader that automatically loads said polymeric capsule into said injection chamber.

\* \* \* \* \*